United States Patent
Modgil et al.

(10) Patent No.: US 6,681,454 B2
(45) Date of Patent: Jan. 27, 2004

(54) APPARATUS AND METHOD FOR SECURING AN OXIMETER PROBE TO A PATIENT

(75) Inventors: Onkar S. Modgil, Plano, TX (US); Christopher G. Chin, Granada Hills, CA (US)

(73) Assignee: UDT Sensors, Inc., Hawthorne, CA (US)

( * ) Notice: Subject to any disclaimer, the term of this patent is extended or adjusted under 35 U.S.C. 154(b) by 126 days.

(21) Appl. No.: 10/072,392

(22) Filed: Feb. 5, 2002

(65) Prior Publication Data

US 2002/0116797 A1 Aug. 29, 2002

Related U.S. Application Data

(63) Continuation of application No. 09/506,467, filed on Feb. 17, 2000, now Pat. No. 6,385,821.

(51) Int. Cl.[7] ............................................. A44B 21/00
(52) U.S. Cl. ................................................. 24/306; 24/304
(58) Field of Search ........................ 24/306, 450, 304, 24/442, 16 R, DIG. 11; 128/880, DIG. 15, DIG. 26; 439/369, 371; 137/375; 600/322, 323, 340, 344, 379, 384, 386; 429/99–100; 248/205.2, 68.1, 74.3; 604/179, 180

(56) References Cited

U.S. PATENT DOCUMENTS

| | | |
|---|---|---|
| 2,253,108 A | 8/1941 | Casey, Jr. |
| 2,985,552 A | 5/1961 | Watanabe |
| 3,232,289 A | 2/1966 | Zimmerman |
| 4,114,838 A | 9/1978 | Knauf |
| 4,530,350 A | 7/1985 | Brown et al. |
| 4,730,610 A * | 3/1988 | Graebe ........................ 128/882 |
| 4,825,879 A | 5/1989 | Tan et al. |
| 4,865,038 A | 9/1989 | Rich et al. |
| 4,926,501 A | 5/1990 | Goosen |
| 5,131,118 A | 7/1992 | Breeher |
| 5,147,216 A | 9/1992 | Shotey |
| 5,209,230 A | 5/1993 | Swedlow et al. |
| 5,339,810 A | 8/1994 | Ivers et al. |
| 5,368,025 A | 11/1994 | Young et al. |
| 5,437,275 A | 8/1995 | Amundsen et al. |
| 5,715,535 A | 2/1998 | Hamilton et al. |
| 5,742,945 A | 4/1998 | Lindaman |
| 5,830,136 A | 11/1998 | Delonzor et al. |
| RE36,000 E | 12/1998 | Swedlow et al. |
| 5,919,133 A | 7/1999 | Taylor et al. |
| 5,925,027 A | 7/1999 | Schmitz |
| 6,385,821 B1 * | 5/2002 | Modgil et al. ................ 24/306 |

* cited by examiner

*Primary Examiner*—James R. Brittain
(74) *Attorney, Agent, or Firm*—Jones Day

(57) ABSTRACT

A strap or fastener for removably securing an oximeter probe to the appendage of a patient. The strap is made of an elastic material that wraps around the outside of the oximeter probe and is secured to the oximeter probe by attachment mechanisms such as Velcro that can be readjusted after initial application without producing excessive stress on the spring hinge of the oximeter probe.

24 Claims, 5 Drawing Sheets

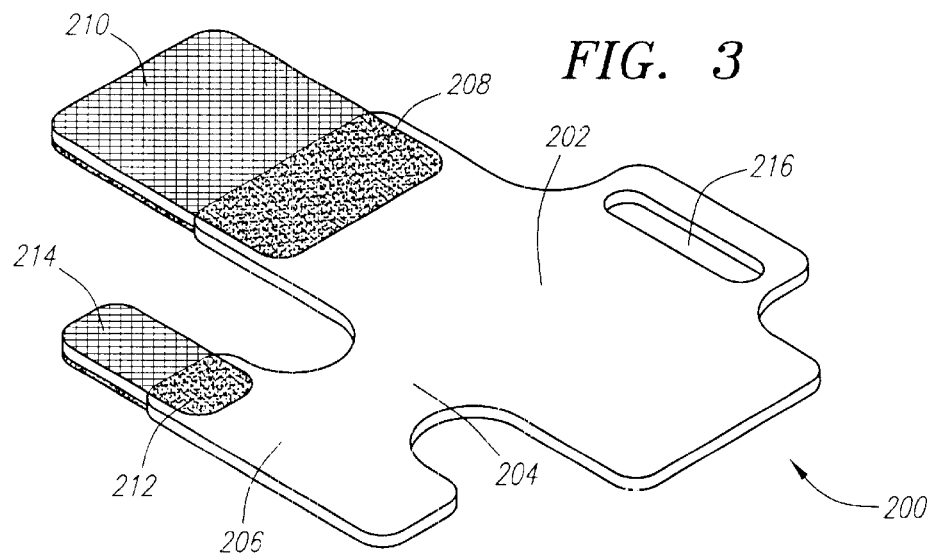
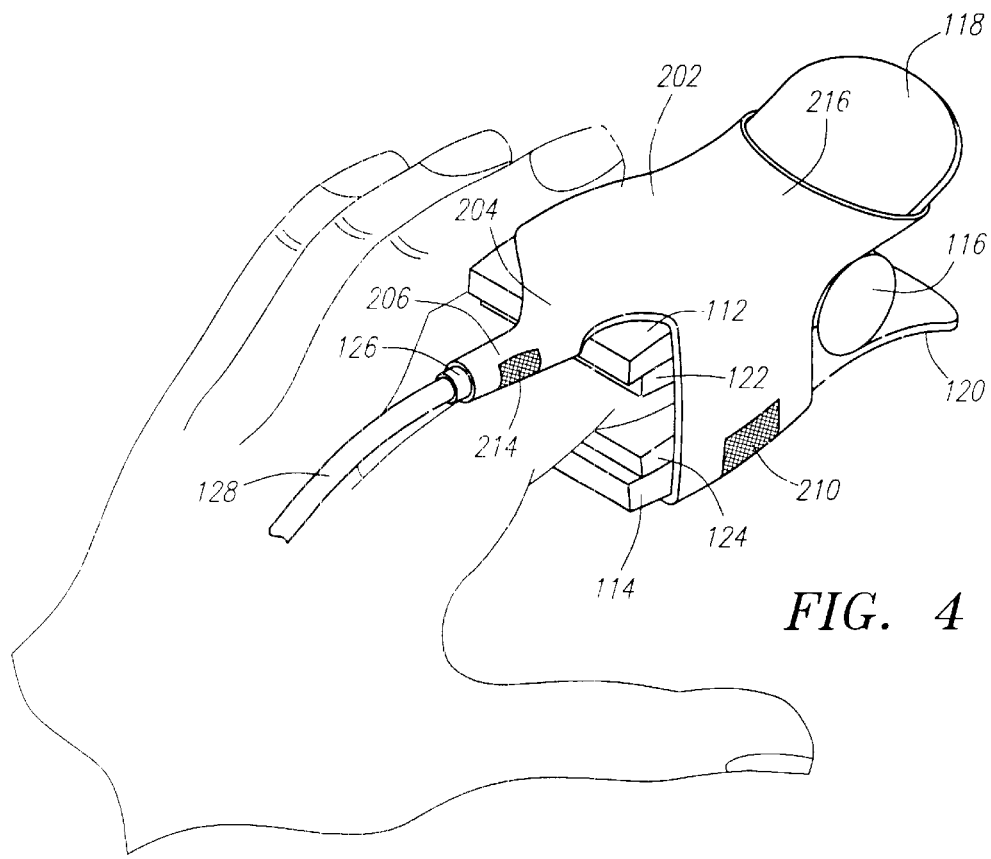

APPARATUS AND METHOD FOR SECURING AN OXIMETER PROBE TO A PATIENT

This application is a continuation of U.S. patent application Ser. No. 09/506,467, filed Feb. 17, 2000, now U.S. Pat. No. 6,385,821 which is herein incorporated by reference.

BACKGROUND OF THE INVENTION

The present invention relates to medical sensors for detecting physiological functions and, in particular, to an apparatus for securing an oximeter probe to an appendage of a patient.

Pulse oximetry is a non-invasive medical technique useful for measuring certain vascular conditions. A pulse oximetry system comprises a sensor appliance containing a light source, such as an L.E.D., and a light sensor, such as a photodetector, and is mounted to the finger, toe or earlobe of a patient. The oximetry sensor emits light, which is scattered through a portion of the patient's tissue where blood perfuses the tissue and the light sensor photoelectrically senses the absorption of light in such tissue. The measurement of light absorbed is used to evaluate various characteristics of a patient such as oxygen saturation of hemoglobin in arterial blood, the volume of individual blood pulsations supplying the tissue, and the rate of blood pulsations corresponding to each heartbeat of a patient.

One kind of commonly used oximetry probe 110 is illustrated in FIGS. 1 and 2. The probe 110 comprises first and second outer shells 112, 114, a spring hinge 116 at the distal end of the probe 110, first and second extending tabs 118, 120, first and second inner pads 122, 124, and a cord 128 connected to the proximal end of the probe. FIG. 1 depicts the oximeter probe 110 in use. The first and second outer shells 112, 114 are separated by forcing the first and second extending tabs 118, 120 toward one another. The patient's finger or other appendage is then slipped between the first and second inner pads 122, 124. On the exposed faces of the first and second inner pads 122, 124 are the photoemitter and photodetector used to measure various vascular conditions of the patient. The data from the photodetector is then transmitted to an attached console electrical cord 128.

The spring hinge 116 is soft because excessive pressure on the finger can distort pulsations in the finger's blood supply. As a result, oximetry sensors frequently fall off the patient's finger when the patient is allowed to move unrestrained.

To prevent excessive movement of a finger to which the probe 110 is attached, medical personnel may secure the hand or arm to the patient's bed or a stationary object located nearby. A patient would be allowed to move the arm and hand more freely so that discomfort to the patient is avoided. To allow for the patient to move freely while not compromising the security of the oximeter probe 110 upon the finger, an additional means of securing the probe 110 to the patient is necessary.

Further, even small movements by the patient can cause differential motion between the oximeter probe 110 and the patient because the physical construction of the sensors renders them bulky and difficult to securely fasten to a patient's appendage. Such differential motion causes the signal received by the light sensor to be distorted, resulting in inaccurate measurements of the amount of blood constituent being evaluated.

In practice, reusable oximeter probes are frequently secured to the patient's appendage using adhesive tape. This method requires that the adhesive tape be applied such that sufficient pressure is applied to the patient's finger to securely fasten the oximeter probe 110, but not so much that vasoconstriction occurs. If the practitioner creates too much or too little pressure during the initial application of the adhesive tape, it becomes necessary to remove the adhesive tape from the body of the oximeter probe 110 and replace it in a different position. Such readjustment is made difficult by the bond between the tape and the shell of the oximeter probe 110. In addition, the residual adhesive remaining on the shell increases risk of contamination. Further, if the tape is in contact with both the patient's skin and the oximeter probe 110, removal of the adhesive tape from the patient's skin can cause irritation, especially when the patient's skin is particularly sensitive due to trauma or age.

Often, when adhesive tape is used to secure an oximeter probe to the appendage of the patient, the adhesive tape stresses the structure of the oximeter probe. Such distortion occurs if the adhesive tape is not applied with substantially equal pressure on both side openings of the oximeter probe. The undue stress on the spring mechanism that results from such distortion shortens the useful life span of the oximeter probe. Additionally, use of adhesive tape to secure the oximeter probe to the patient also decreases the useful life span of the oximeter probe by making sterilization of the oximeter probe after each use difficult because of adhesive build up. When adhesive tape is removed from the oximeter probe, residue of the adhesive remains on the shell of the probe. Removing the residue may require vigorous scrubbing and/or use of abrasive cleaning agents.

Another concern when securing an oximeter probe to a patient is ensuring that ambient light does not interfere with the signal being received by the photodetector. Outside light is easily scattered and transmitted within the tissue toward the photodetector because skin tissue is translucent. This ambient light causes interference with the signal detected at the photodetector.

Further, vasoconstriction may also be caused by exposure of the appendage to the often cool outside air. Low temperature induced vasoconstriction and the resultant decrease in blood supply may significantly affect the performance of the oximeter probe. Conventional attempts to alleviate the problem of low temperature vasoconstriction include using an integral heater with the sensor and periodic massaging. Heaters, however, must be well regulated to avoid overheating. Furthermore, they increase the complexity of the sensor and can be costly. Periodic massaging can be effective, but usually requires removal of the probe while the appendage is massaged. After some massaging of the appendage to stimulate blood flow to it, the probe is reapplied and measurement resumed. It would be desirable to employ a less complex, passive means for retaining body heat that does not interrupt the measurement process.

SUMMARY OF THE INVENTION

The present invention is preferably a strap for securing an oximeter probe to an appendage of a patient. The strap is preferably made of elastic material and may be removably secured to the outside of an oximeter probe to allow for readjustment of the strap after initial application without producing excessive stress on the spring hinge of the oximeter probe.

In one embodiment, the strap is preferably a patch of material comprising a body, a tab located at a proximal end of the body and connected to the body of the strap by a narrow neck, an attachment mechanism for securing the body of the strap about an oximeter probe, and another attachment mechanism for securing the tab about the cord of an oximeter probe. Preferably, at a distal end of the body of the strap is a flap that has a slit through which the extending flap of the top shell of the oximeter probe may be placed to prevent excessive longitudinal movement of the strap.

In another embodiment of the present invention, the strap is preferably a patch of material comprising a body, a tab located at a proximal end of the body and connected to the body of the strap by a narrow neck, one attachment mechanism for securing the body of the strap, a second attachment mechanism for securing the tab and a third attachment mechanism preferably substantially perpendicular to the first and second attachment mechanisms for preventing excessive longitudinal movement of the strap.

In yet another embodiment of the strap, the strap preferably comprises two flaps connected by a neck, one of the flaps having a tab. The strap is secured to the oximeter probe by placing the flaps on opposing sides of the oximeter probe and placing the neck along the spring hinge at the distal end of the oximeter probe. An attachment mechanism is wrapped around the strap enclosing the body of the oximeter probe to secure the probe to an appendage of a patient while a second attachment mechanism is wrapped around the tab of the strap enclosing the cord neck of the oximeter probe to prevent excessive longitudinal movement of the strap.

In yet another embodiment of the present invention the strap is preferably conformed as a sock which, in use, is slipped over the oximeter probe. The strap further comprises two attachment mechanisms. One attachment mechanism is wrapped around the strap about the body of the oximeter probe so that the spring hinge is appropriately compressed on the appendage of the patient. The other is wrapped around the strap enclosing the cord neck of the oximeter probe.

For a fuller understanding of the nature of the present invention, reference should be made to the ensuing detailed description taken in conjunction with the accompanying drawings.

BRIEF DESCRIPTION OF THE DRAWINGS

In the drawings:

FIG. 3 is a perspective view of a preferred embodiment of the oximeter probe strap according to the present invention.

FIG. 4 is a perspective view, from the proximal end of the oximeter probe, of the strap depicted in FIG. 3 in use.

DETAILED DESCRIPTION OF THE PREFERRED EMBODIMENTS

Figure 1:
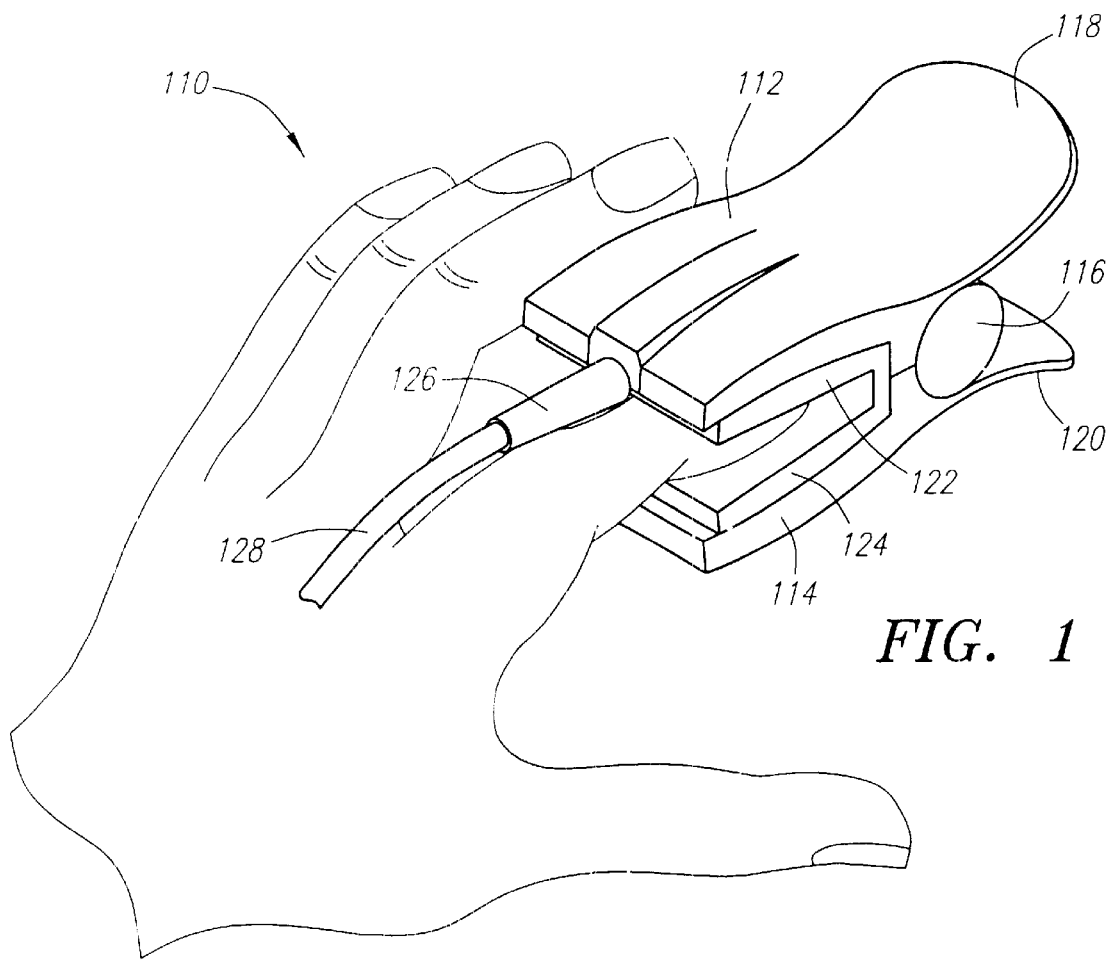
FIG. 1 is a perspective view from the proximal end of an oximeter probe.
Figure 2:
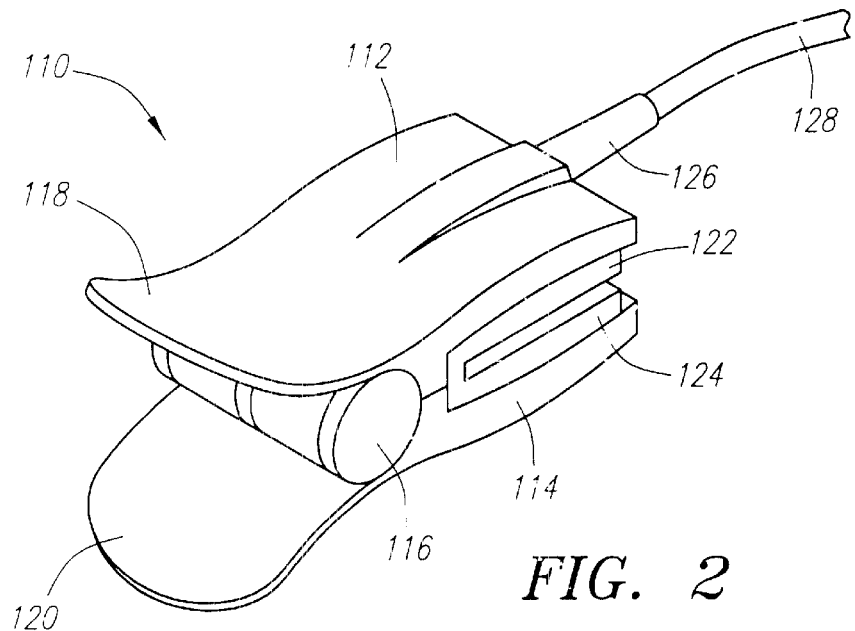
FIG. 2 is a perspective view from the distal end of an oximeter probe.

FIGS. 1 and 2 illustrate a reusable oximeter probe 110 commonly used in the medical industry. FIG. 1 is a perspective view taken from the proximal end of the oximeter probe 110 while attached to a patient. FIG. 2 depicts the oximeter probe 110 from the distal end in its neutral position.

The oximeter probe 110 comprises a first and second outer shell 112, 114, a spring hinge 116 at the distal end of the probe, first and second extending tabs 118, 120, first and second inner pads 122, 124, a cord sleeve 126, and a cord 128. FIG. 1 depicts the oximeter probe in use. The first and second outer shells 112, 114 are separated by pressing the first and second extending tabs 118, 120 toward one another. The patient's finger or other appendage is then slipped between the first and second inner pads 122, 124. On the inside faces of the first and second inner pads 122, 124 are a photoemitter and a photodetector (not shown) used to measure various vascular conditions of the patient. The data from the photodetector is then transmitted to an attached console via the cord 128.

FIG. 3 is a perspective view of a preferred embodiment of an oximeter probe strap comprising a body 202, a tab 206 located at the proximal end of the body 202, a first attachment mechanism 210 for securing the body 202 of the strap 200, and a second attachment mechanism 214 for securing the tab 206. The tab 206 is preferably connected to the body 202 of the strap 200 by a preferably narrow strip 204, the body 202, tab 206, and strip 204 preferably constituting a single patch of elastic material.

The strap may also include a flap 218 at the end opposing the strip 204, the flap 218 having a slit 216 through which the extending tab 118 of the top shell 112 of the oximeter probe 110 may be placed, as shown in FIG. 4. It is preferrable that the strap 200 include the flap 218 with the slit 216 so that longitudinal movement of the strap 200 along the hard outer shells 112, 114 of the oximeter probe 110 may be minimized.

The strap 200 preferably has a total length (from proximal to distal end) of approximately 3.0 inches. The width of the body 202 preferably is approximately 3.5 inches and the width of the tab 206 preferably is approximately 1.25 inches. The body 202 and the tab 206 constitute one patch of elastic material that is preferably composed of a foam laminate with brushed nylon that is hook engagable.

As illustrated in FIG. 4, on a surface of the body 202 of the strap 200 is the first attachment mechanism 210 for securing the strap 200 about the oximeter probe 110 such that the spring hinge 116 of the oximeter probe 110 is appropriately compressed to maintain secure contact between the inner surfaces 122, 124 of the oximeter probe 110 and the appendage of the patient. The first attachment mechanism 210 preferably is comprised of a patch of hook material, such as Velcro, which may be adhesively laminated 210 to the material of the strap 200 as shown in FIG. 3. Alternatively, the first attachment mechanism 210 may be comprised of adhesive strip or a patch of hook material separate from the strap 200.

On a surface of the tab 206 is a second attachment mechanism 214 for holding the strap 200 about the cord sleeve 126 of the oximeter probe 110. Like the first attachment mechanism 210, the second attachment mechanism 214 preferably comprises a patch of hook material, such as Velcro, which may be adhesively laminated 212 to the tab 206 as shown in FIG. 3. Alternatively, the second attachment mechanism 214 may constitute an adhesive strip or a patch of hook material separate from the strap 200.

In use, after the patient's appendage is secured in the probe 110, the body 202 of the strap 200 may be placed over the top portion of the hard shell 112 of the oximeter probe 110 with the extending tab 118 of the top portion of the hard shell placed through the slit 216 in the flap 218 of the strap 200. The first attachment mechanism 210 may be wrapped around the outer surface of the body 202 of the strap 200 enclosing the upper and lower hard shells 112, 114 of the oximeter probe 110. The second attachment mechanism 214 may be wrapped around the tab 206, enclosing the cord sleeve 126 of the oximeter probe 110.

When hook material is used for the first and second attachment mechanisms 210, 212, the attachment mechanisms can be secured directly to the elastic material that constitutes the strap 200. When adhesive strips are used for the attachment mechanisms 210, 212 the strips may be placed around the entire circumference so that the opposing ends of the adhesive strips overlap to allow for a secure bond. Using hook material as the attachment mechanism may be preferred over an adhesive strip because it may facilitate to a greater degree readjustment of the first attachment mechanism 210 about the strap 200 and the oximeter probe 110.

The combination of the slit 216 in the body 202 of the strap 200 and the second attachment mechanism 214 wrapped around the tab 206 enclosing the cord sleeve 126 prevents excessive longitudinal movement of the strap 200 along the hard shells 112, 114 of the oximeter probe 110. Likewise, the attachment mechanism 210 of the body 202 of the strap 200 holds the oximeter probe 110 securely to the appendage of the patient by reinforcing the spring action of the spring hinge 116.

Figure 5:
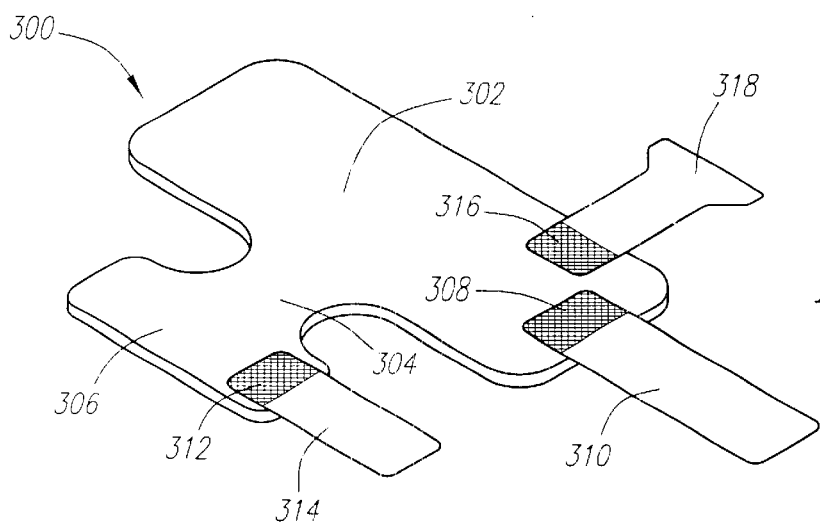
FIG. 5 is a perspective view of a second preferred embodiment of the oximeter probe strap according to the present invention.
Figure 6:
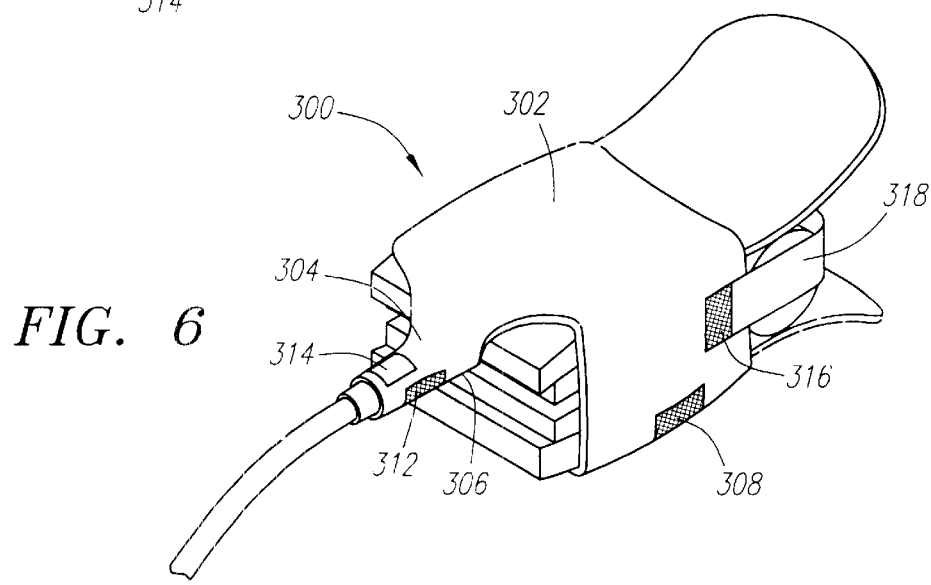
FIG. 6 is a perspective view, from the proximal end of the oximeter probe, of the strap depicted in FIG. 5 in use.
Figure 7:
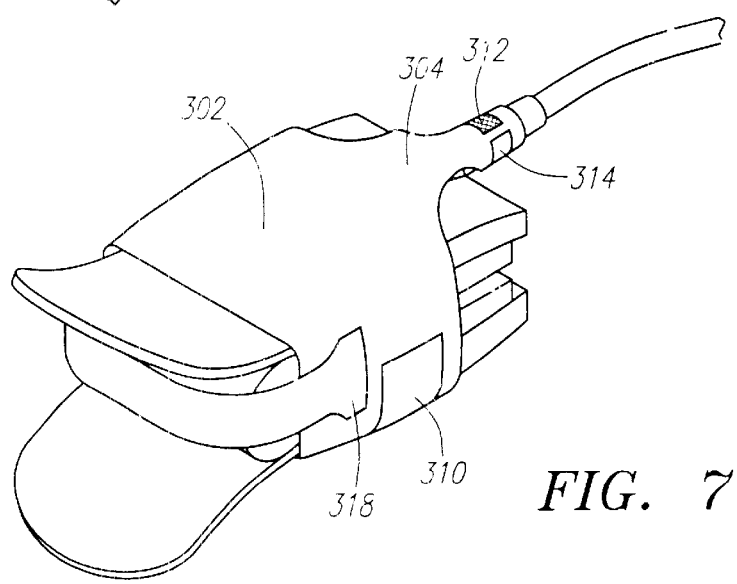
FIG. 7 is a perspective view, from the distal end of the oximeter probe, of the strap depicted in FIG. 5 in use.

FIGS. 5–7 illustrate an alternative preferred embodiment of an oximeter probe strap. FIG. 5 is a perspective view of a strap 300 alone. FIG. 6 depicts the strap 300 in use as viewed from the proximal end of the oximeter probe 110. FIG. 7 shows the strap 300 in use as viewed from the distal end of the oximeter probe 110. As shown in FIG. 5, strap 300 is illustrated to have some of the same components as strap 200. Numbers with identical second and third digits represent corresponding components.

The body 312 of the strap 300 preferably does not have a slit 216 as does the strap 200 depicted in FIG. 3. Instead, a third attachment mechanism 318 is attached to the body 302 of the strap 300 such that it preferably wraps around the distal end of the oximeter probe 110 and is attached to the opposite side of the body 302 of the strap 300 as shown in FIGS. 6–7.

The attachment mechanisms 310, 314, 318 are preferably comprised of a patch of hook material, such as Velcro, which may be adhesively laminated 308, 312, 316 to the material of the strap 300 as shown in FIG. 5. Alternatively, the attachment mechanisms 310, 314, 318 are comprised of an adhesive strip or a patch of hook material separate from the strap 300.

Referring to FIGS. 6–7, the body 302 of the strap 300 is placed over the top portion of the hard shell 112 of the oximeter probe 110. The first attachment mechanism 310 may be wrapped around the outer surface of the body 302 of the strap enclosing the upper and lower hard shells 112, 114 of the oximeter probe 110. The second attachment mechanism 314 of the tab 306 may be wrapped around the tab 306, enclosing the cord sleeve 126 of the oximeter probe 110. As illustrated in FIGS. 6–7, the third attachment mechanism 318 is attached 316 to the body 302 of the strap 300, wrapped around the distal end of the oximeter probe 110 and attached to the body 302 of the strap 300 on the opposite side of the probe 110.

The second attachment mechanism 314 may be placed around the tab 306 enclosing the cord sleeve 126 and the third attachment mechanism 318 may be placed around the distal end of the oximeter probe 110 to prevent excessive longitudinal movement of the strap 300 along the hard shells 112, 114 of the oximeter probe 110. Likewise, the first attachment mechanism 310 of the body 302 of the strap 300 holds the oximeter probe securely to the appendage of the patient by reinforcing the spring action of the spring hinge 116.

Figure 8:
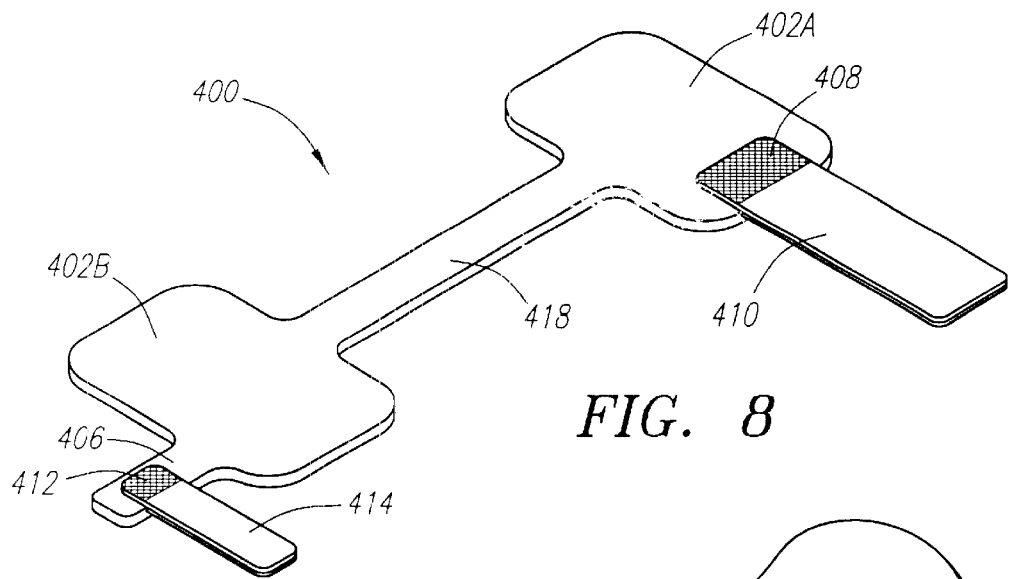
FIG. 8 is a perspective view of a third preferred embodiment of the oximeter probe strap according to the present invention.
Figure 9:
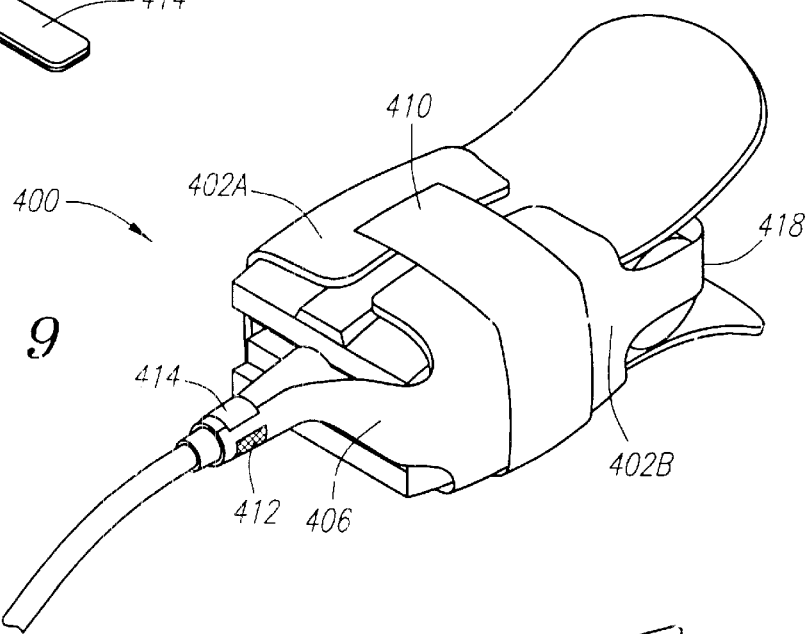
FIG. 9 is a perspective view, from the proximal end of the oximeter probe, of the strap depicted in FIG. 8 in use.
Figure 10:
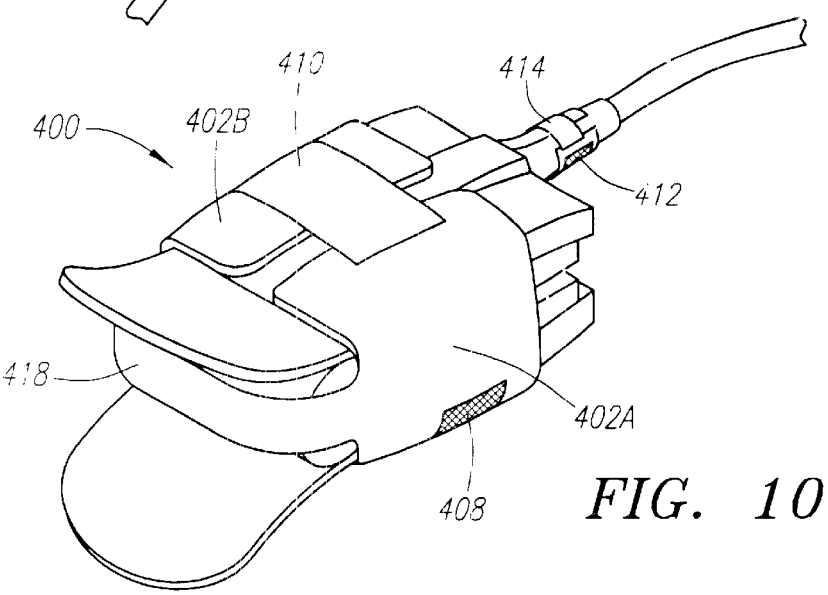
FIG. 10 is a perspective view, from the distal end of the oximeter probe, of the strap depicted in FIG. 8 in use.

Another preferred embodiment is shown in FIGS. 8–10. This embodiment of the oximeter probe strap 400 is comprised of a first flap 402A and a second flap 402B, a tab 406, a connecting neck 418, a first attachment mechanism 410 and a second attachment mechanism 414. The first flap 402A and the second flap 402B are at opposite ends of the neck portion 418 of the strap 400. The first attachment mechanism 410 attaches to the first flap 402A and the second attachment mechanism attaches to the tab 406.

In use, the first flap 402A of the strap 400 is placed along the side of the oximeter probe 110 where the upper and lower shells 112, 114 meet. The neck 418 of the strap 400 wraps around the distal end of the oximeter probe 110 and the second flap 402B is placed along the side of the oximeter probe 110 where the upper and lower shells 112, 114 meet, opposite the first flap 402A. The first attachment mechanism 410 is wrapped around the surface of the first and second flaps 402A, 402B, such that the spring hinge 116 of the oximeter probe 110 is secured in an appropriately compressed position. The second attachment mechanism 414 is wrapped around the surface of the tab 406 enclosing the cord sleeve 126 of the oximeter probe 110.

The first and second attachment mechanisms 410, 414 preferably are comprised of a patch of hook material, such as Velcro, which may be adhesively laminated 408, 412 to the material of the strap 400 as shown in FIG. 8. Alternatively, the first and second attachment mechanisms 408, 412 are comprised of an adhesive strip or a patch of hook material separate from the strap 400. If an adhesive strip is used, it is preferably wrapped completely around the surface of the strap 400 such that opposing ends of the adhesive strip overlap to ensure a secure bond. The use of hook material for the first and second attachment mechanisms 410, 414 is preferred to facilitate readjustment of the attachment mechanisms 410, 414.

Figure 11:
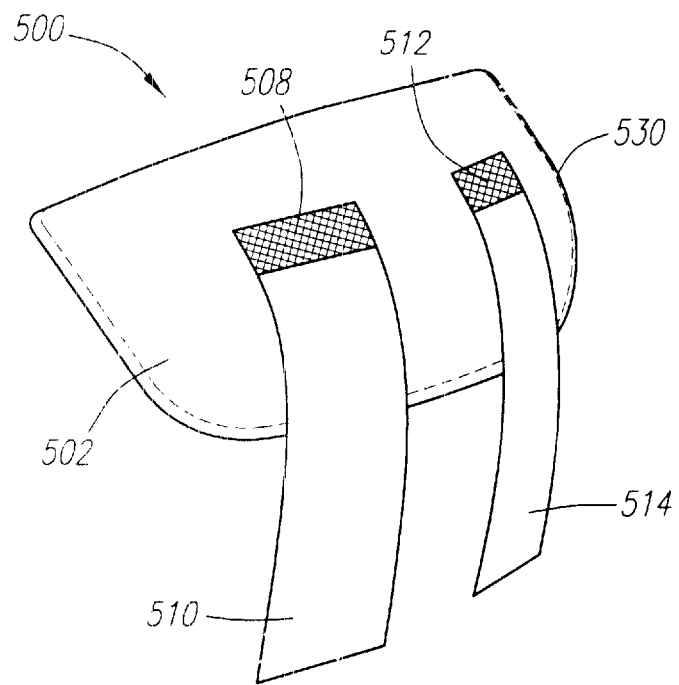
FIG. 11 is a perspective view of a fourth preferred embodiment of the oximeter probe strap according to the present invention.
Figure 12:
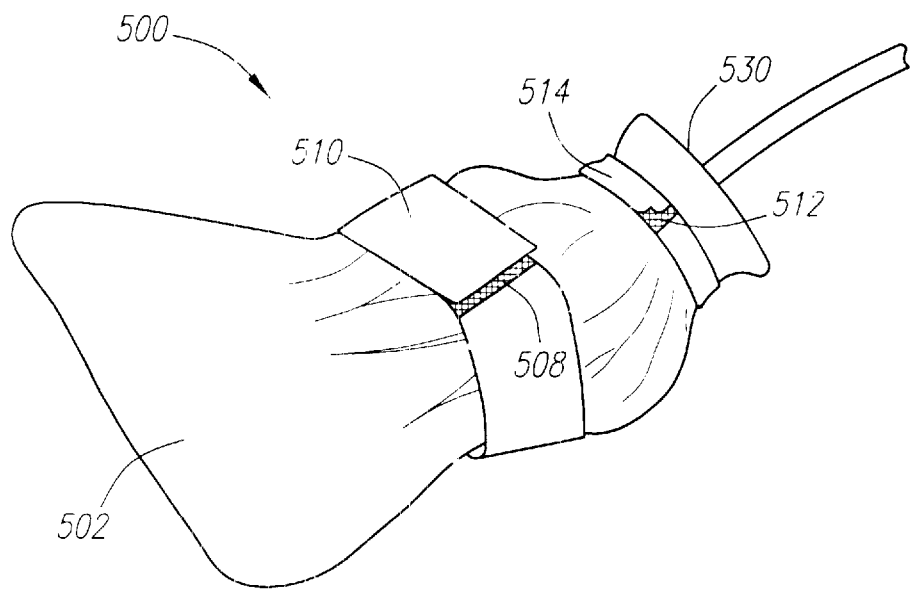
FIG. 12 is a perspective view, from the distal end of the oximeter probe, of the strap depicted in FIG. 11 in use.

Another preferred embodiment is shown in FIGS. 11–12. This embodiment of the oximeter probe strap 500 is preferably comprised of at least one patch of fabric 502 in a sock-like apparatus with an opening 530, a first attachment mechanism 510 and a second attachment mechanism 514.

FIG. 12 depicts the strap 500 in use. The strap 500 may be slid over the oximeter probe 110 such that the body of the probe enclosing the patient's appendage is inside the fabric 502 and the cord 128 exits the strap 500 through the strap opening 530. The first attachment mechanism 510 may be wrapped around the surface of the fabric 502 as a girth enclosing the first and second outer shells 112, 114, the spring hinge 116 and the first and second extending tabs 118, 120 of the oximeter probe strap 110 such that the spring hinge 116 of the oximeter probe 110 is secured in an appropriately compressed position about the patient's appendage. The second attachment mechanism 514 is wrapped around the fabric 502 enclosing the cord sleeve 126 of the oximeter probe 110.

The first and second attachment mechanisms 510, 514 preferably are comprised of a patch of hook material, such as Velcro, which may be adhesively laminated 508, 512 to the material of the strap 502 as shown in FIG. 11. Alternatively, the first and second attachment mechanisms 508, 512 are comprised of an adhesive strip or a patch of hook material separate from the strap 500. If an adhesive strip is used, it is preferably wrapped completely around the surface of the strap 500 such that opposing ends of the adhesive strip overlap to ensure a secure bond. The use of hook material for the first and second attachment mechanisms 510, 514 is preferred to facilitate readjustment of the attachment mechanisms 510, 514.

As will be understood by those skilled in the art, the present invention may be embodied in other specific forms without departing from the essential characteristics thereof. Accordingly, the foregoing description is illustrative of the invention, but not limiting to the scope of the invention, which is set forth in the following claims.

What is claimed is:

1. A strap for an oximeter probe, comprising:
   a patch having a first flap, a second flap, an elongated neck joining said first flap and said second flap, and a tab connected to said second flap;
   a first attachment mechanism for removably securing said first and second flaps to outer shells of the oximeter probe; and
   a second attachment mechanism for removably securing said tab to a cord of the oximeter probe.

2. The strap of claim 1 wherein said first attachment mechanism is substantially perpendicular to said neck.

3. The strap of claim 1 wherein said first attachment mechanism is substantially parallel to said second attachment mechanism.

4. A strap for an oximeter probe, comprising:
   a patch having a first flap, a second flap, a neck joining said first flap and said second flap, and a tab connected to said second flap;
   a first attachment mechanism for removably securing said first and second flaps to outer shells of the oximeter probe; and
   a second attachment mechanism for removably securing said tab to a cord of the oximeter probe;
   wherein said patch comprises an elastic hook engagable material.

5. The strap of claim 4, said elastic hook engagable material comprising foam laminate with a brushed nylon surface.

6. A strap for an oximeter probe, comprising:
   a patch having a first flap, a second flap, a neck joining said first flap and said second flap, and a tab connected to said second flap;
   a first attachment mechanism for removably securing said first and second flaps to outer shells of the oximeter probe; and
   a second attachment mechanism for removably securing said tab to a cord of the oximeter probe;
   wherein said flaps are approximately 1.5 inches square and said neck is approximately 1.5 inches in length.

7. The strap of claim 1 wherein said first and second attachment mechanisms are comprised of hook material.

8. A strap for an oximeter probe, comprising:
   a patch having a first flap, a second flap, a neck joining said first flap and said second flap, and a tab connected to said second flap;
   a first attachment mechanism for removably securing said first and second flaps to outer shells of the oximeter probe; and
   a second attachment mechanism for removably securing said tab to a cord of the oximeter probe;
   wherein said first and second attachment mechanisms are comprised of hook material, and at least one of the attachment mechanisms is adhesively laminated to said patch.

9. A strap for an oximeter probe, comprising:
   a patch having a first flap, a second flap, a neck joining said first flap and said second flap, and a tab connected to said second flap;
   a first attachment mechanism for removably securing said first and second flaps to outer shells of the oximeter probe; and
   a second attachment mechanism for removably securing said tab to a cord of the oximeter probe;
   wherein said first and second attachment mechanisms are adhesive strips.

10. A strap for an oximeter probe, comprising:
    a patch having a first flap, a second flap, a neck joining said first flap and said second flap, and a tab connected to said second flap;
    a first attachment mechanism for removably securing said first and second flaps to outer shells of the oximeter probe; and
    a second attachment mechanism for removably securing said tab to a cord of the oximeter probe;
    wherein said tab extends substantially parallel to said neck.

11. The strap of claim 1 wherein said second attachment mechanism is substantially perpendicular to said neck.

12. A strap for an oximeter probe, comprising:
    a patch having a first flap, a second flap, a neck joining said first flap and said second flap, and a tab connected to said second flap;
    a first attachment mechanism for removably securing said first and second flaps to outer shells of the oximeter probe; and
    a second attachment mechanism for removably securing said tab to a cord of the oximeter probe;
    wherein said cord is disposed on a proximal end of the oximeter probe and said neck is sized to wrap around a distal end of the oximeter probe.

13. A strap for an oximeter probe, comprising:
    a patch having a first flap sized to be removably secured to a first portion of an oximeter probe, a second flap sized to be removably secured to a second portion of an oximeter probe, and a neck joining said first flap and said second flap, said neck sized to wrap around a distal end of the oximeter probe; and
    a first attachment mechanism for removably securing said first and second flaps to first and second portions of the oximeter probe.

14. The strap of claim 13 wherein said first and second portions of the oximeter probe overlap.

15. The strap of claim 13 further comprising a tab connected to one of said first and second flaps and a second attachment mechanism for removably securing said tab to a cord on a proximal end of the oximeter probe.

16. A strap for an oximeter probe, comprising:
    a patch having a first flap sized to be removably secured to a first portion of an oximeter probe, a second flap sized to be removably secured to a second portion of an oximeter probe, and a neck joining said first flap and said second flap, said neck sized to wrap around a distal end of the oximeter probe;

a first attachment mechanism for removably securing said first and second flaps to first and second portions of the oximeter probe; and a tab connected to one of said first and second flaps and a second attachment mechanism for removably securing said tab to a cord on a proximal end of the oximeter probe;

wherein said tab extending substantially parallel to said neck.

17. A strap for an oximeter probe, comprising:

a patch having a first flap sized to be removably secured to a first portion of an oximeter probe, a second flap sized to be removably secured to a second portion of an oximeter probe, and a neck joining said first flap and said second flap, said neck sized to wrap around a distal end of the oximeter probe; and a first attachment mechanism for removably securing said first and second flaps to first and second portions of the oximeter probe;

wherein the first and second flaps comprise an elastic hook engagable material.

18. The strap of claim 17 wherein the elastic hook engagable material comprises foam laminate with a brushed nylon surface.

19. The strap of claim 13 wherein one of said the first and second attachment mechanism comprises hook material.

20. The strap of claim 1 wherein said first and second flaps are approximately the same size.

21. The strap of claim 1 wherein said neck has a length that is approximately the magnitude of a surface area of said first flap.

22. The strap of claim 13 wherein said first and second flaps are approximately the same size.

23. The strap of claim 13 wherein said neck has a length that is approximately the magnitude of a surface area of said first flap.

24. The strap of claim 13 wherein said first flap is approximately 1.5 inches square and said neck is approximately 1.5 inches in length.

* * * * *